United States Patent [19]

Sih

[11] 4,273,718
[45] Jun. 16, 1981

[54] 2-DECARBOXY-2-HYDROXYMETHYL-9-DEOXY-6ϵ,9αEPOXY-16,16-DIFLUORO-19-HYDROXY-PGF$_1$

[75] Inventor: John C. Sih, Portage, Mich.

[73] Assignee: The Upjohn Company, Kalamazoo, Mich.

[21] Appl. No.: 126,483

[22] Filed: Mar. 3, 1980

Related U.S. Application Data

[62] Division of Ser. No. 054,811, Jul. 5, 1979, Pat. No. 4,225,508.

[51] Int. Cl.$^3$ .......................................... C07D 307/935
[52] U.S. Cl. ................................................. 260/346.22
[58] Field of Search .................... 260/346.22, 346.73; 542/416, 420, 421, 426; 548/250

[56] References Cited

U.S. PATENT DOCUMENTS

| 3,878,046 | 4/1975 | Marsheck et al. ................... 562/503 |
| 4,054,595 | 10/1977 | Marx et al. ........................... 562/503 |

FOREIGN PATENT DOCUMENTS

| 862514 | 4/1978 | Belgium ............................ 260/346.22 |
| 777401 | 12/1977 | South Africa . | |

*Primary Examiner*—Henry R. Jiles
*Assistant Examiner*—Bernard Dentz
*Attorney, Agent, or Firm*—Robert A. Armitage

[57] ABSTRACT

The present invention provides novel 19-Hydroxy-PGI$_1$ compounds which are useful for pharmacological purposes, e.g., anti-asthmatic indications.

1 Claim, No Drawings

2-DECARBOXY-2-HYDROXYMETHYL-9-DEOXY-6ε,9αEPOXY-16,16-DIFLUORO-19-HYDROXY-PGF$_1$

CROSS REFERENCE TO RELATED APPLICATION

The present invention is a divisional application of United States Ser. No. 054,811, filed July 5, 1979, now U.S. Pat. No. 4,225,508.

BACKGROUND OF THE INVENTION

The present invention provides novel prostacyclin analogs. Particularly, the present invention relates to prostacyclin analogs substituted at the C-19 position by hydroxy.

Particularly, the present invention relates to 19-hydroxy-PGI$_1$ compounds. The novel prostacyclin analogs are useful for pharmacological purposes, e.g., as anti-asthmatic agents. The preparation and use of these compounds is incorporated here by reference from U.S. Pat. No. 4,225,508.

PRIOR ART

For background on prostacyclin, see for example R. A. Johnson, et al., Prostaglandins 12, 915–928 (1976) and R. A. Johnson, et al., J. Am. Chem. Soc. 100, 7690–7704 (1978), and, as to pharmacological activity, the references cited therein. For analogs of prostacyclin, see, for example, J. Fried, et al., Proc. Natl. Acad. Sci. U.S.A. 74, 2199–2203, K. C. Nicolaou, et al., J.C.S. Chem Comm. 1977, 331–332, N. A. Nelson, J. Am. Chem. Soc. 99, 7362–7363 (1977), and K. Kojima, et al., Tetra. Letters, 1978, (1977), and K. Kojima, et al., Tetra. Letters, 1978, 3743–3746. Regarding the nomenclature for analogs of PGI$_2$, see R. A. Johnson, et al., Prostaglandins 15, 737–740 (1978).

SUMMARY OF THE INVENTION

The present invention particularly provides a prostacyclin-type compound of the formula

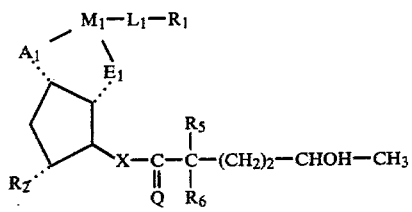

wherein A$_1$ is —O— (oxa) and E$_1$ is —CH$_2$
wherein L$_1$ is
(1) —(CH$_2$)$_n$—, wherein n is one to 5, inclusive,
(2) —(CH$_2$)$_p$—CF$_2$—, wherein p is 2, 3, or 4, or
(3) —CH$_2$—CH=CH—;
wherein M$_1$ is

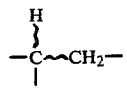

wherein Q is oxo, α-H:β-H, α-OH:β-R$_4$, or α-R$_4$:β-OH,
wherin R$_4$ is hydrogen or alkyl of one to 4 carbon atoms, inclusive,
wherein R$_1$ is
(1) —COOR$_3$,
(2) —CH$_2$OH,
(3) —CH$_2$N(R$_7$)(R$_8$),
(4) —CO—N(R$_7$)(R$_8$),
(5) —CO—NH—SO$_2$—R$_{15}$, or
(6) tetrazolyl,
wherein R$_3$ is
(a) hydrogen,
(b) alkyl of one to 12 carbon atoms, inclusive,
(c) cycloalkyl of 3 to 10 carbon atoms, inclusive,
(d) aralkyl of 7 to 12 carbon atoms, inclusive,
(e) phenyl,
(f) phenyl substituted with one, 2, or 3 chloro or alkyl groups of one to 3 carbon atoms, inclusive;
(g) —(p—Ph)—CO—CH$_3$,
(h) —(p—Ph)—NH—CO—(p—Ph)—NH—CO—CH$_3$,
(i) —(p—Ph)—NH—CO—(Ph),
(j) —(p—Ph)—NH—CO—CH$_3$,
(k) —(p—Ph)—NH—CO—NH$_2$,
(l) —(p—Ph)—CH=N—NH—CO—NH$_2$,
(m) β-naphthyl,
(n) —CH$_2$—CO—R$_{16}$,
wherein —(p—Ph)— is para-phenylene and —(Ph) is phenyl;
wherein R$_{16}$ is phenyl, p-bromophenyl, p-biphenylyl, p-nitrophenyl, p-benzamidophenyl, or 2-naphthyl, or
(0) a pharmacologically acceptable cation; wherein R$_7$ and R$_8$ are hydrogen, alkyl of one to 12 carbon atoms, inclusive, benzyl, or phenyl, being the same or different, and wherein R$_{15}$ is hydrogen, alkyl of one to 12 carbon atoms, inclusive, phenyl, phenyl-substituted with one, 2, or 3 chloro or alkyl groups of one to 3 carbon atoms, inclusive, or phenyl substituted with hydroxycarbonyl or alkoxycarbonyl of one to 4 carbon atoms, inclusive, wherein R$_2$ is hydrogen, hydroxyl, or hydroxymethyl, wherein R$_5$ and R$_6$ are hydrogen, alkyl of one to 4 carbon atoms, inclusive, or fluoro, being the same or different, with the proviso that one of R$_5$ and R$_6$ is fluoro when the other is hydrogen or fluoro, and wherein X is
(1) trans—CH=CH—,
(2) cis—CH=CH—,
(3) —C≡C—, or
(4) —CH$_2$CH$_2$—.

DESCRIPTION OF THE PREFERRED EMBODIMENTS

The present invention particularly relates to the following compounds:
2-Decarboxy-2-hydroxymethyl-9-deoxy-6ξ,9α-epoxy-19-hydroxy-PGF$_1$, and
2-Decarboxy-2-hydroxymethyl-9-deoxy-6ξ,9α-epoxy-16,16-difluoro-19-hydroxy-PGF$_1$.

I claim:
1. 2-Decarboxy-2-hydroxymethyl-9-deoxy-6ξ,9α-epoxy-16,16-difluoro-19-hydroxy-PGF$_1$.

* * * * *

UNITED STATES PATENT OFFICE
CERTIFICATE OF CORRECTION

Patent No. 4,273,718          Dated 16 June 1981

Inventor(s) John C. Sih

It is certified that error appears in the above-identified patent and that said Letters Patent are hereby corrected as shown below:

The title should read: 2-Decarboxy-2-Hydroxymethyl-9-Deoxy-6$\xi$,9$\alpha$-Epoxy-16,16-Difluoro-19-Hydroxy-PGF$_1$ Signed and Sealed this Fifteenth Day of September 1981

[SEAL]

Attest:

GERALD J. MOSSINGHOFF

Attesting Officer      Commissioner of Patents and Trademarks